United States Patent [19]
Awaji et al.

[11] Patent Number: 6,150,535
[45] Date of Patent: Nov. 21, 2000

[54] PROCESSES FOR PRODUCING AZETIDINE-2-CARBOXYLIC ACID AND INTERMEDIATES THEREOF

[75] Inventors: Hiroshi Awaji, Kobe; Shingo Matsumoto, Himeji; Kenji Inoue, Kakogawa; Kazuhiko Matsuo, Himeji, all of Japan

[73] Assignee: Kaneka Corporation, Osaka, Japan

[21] Appl. No.: 09/403,545

[22] PCT Filed: Apr. 24, 1998

[86] PCT No.: PCT/JP98/01895

§ 371 Date: Dec. 30, 1999

§ 102(e) Date: Dec. 30, 1999

[87] PCT Pub. No.: WO98/47867

PCT Pub. Date: Oct. 29, 1998

[30] Foreign Application Priority Data

Apr. 24, 1997 [JP] Japan ................................. 9-123390
Dec. 10, 1997 [JP] Japan ................................. 9-362268

[51] Int. Cl.$^7$ .................................................. C07D 205/04
[52] U.S. Cl. ............................................ 548/950; 548/953
[58] Field of Search ..................................... 548/950, 953

[56] References Cited

U.S. PATENT DOCUMENTS 4,855,452  8/1989  Verbrugge et al. ..................... 548/953

FOREIGN PATENT DOCUMENTS

| 49-14457 | 2/1974 | Japan . |
| 59-130861 | 7/1984 | Japan . |
| 59-161354 | 9/1984 | Japan . |
| 61-238991 | 10/1986 | Japan . |
| 62-81367 | 4/1987 | Japan . |

OTHER PUBLICATIONS

Rodebaugh, R. M. et al, "A facile New Synthesis of DL–Azetidine–2–Carboxylic Acid (1A) ", *Journal Of Heterocyclic Chemistry*, vol.6, No. 3, June 1, 1969, 435–437, XP002050008.

Rodebaugh, R.M. et al, "A Facile New Synthesis of DL–Azetidine–2–Carboxylic Acid (1A) ", *Journal of Heterocyclic Chemistry*, vol.6, No. 3, Jun. 1, 1969, 435–437, XP002050008.

Powden, L."Azetidine–2–carboxylic Acid: A new Cyclic Imino Acid Ocurring in Plants ", *The Biochemical Journal*, vol. 64, 1956, 323–332, XP000909526.

*Primary Examiner*—Fiona T. Powers
*Attorney, Agent, or Firm*—Pollock, Vande Sande & Amernick

[57] ABSTRACT

The present invention has its object to provide a process for producing azetidine-2-carboxylic acid and an intermediate thereof, which is efficient and economical and suited for industrial practice.

The present invention is related to a process for producing azetidine-2-carboxylic acid of the following formula (5), which comprises subjecting a 4-oxo-2-azetidinecarboxylic acid derivative represented by the general formula (1) to hydride reduction to give azetidine-2-methanol of the following formula (2), treating the same with an amino-protecting agent to give N-protected azetidine-2-methanol represented by the following general formula (3), treating this with an oxidizing agent to give N-protected azetidine-2-carboxylic acid represented by the following general formula (4) and, further, subjecting the amino-protecting group thereof to elimination.

27 Claims, 8 Drawing Sheets

PROCESSES FOR PRODUCING AZETIDINE-2-CARBOXYLIC ACID AND INTERMEDIATES THEREOF

TECHNICAL FIELD

The present invention relates to a process for producing azetidine-2-carboxylic acid from a 4-oxo-2-azetidinecarboxylic acid derivative via azetidine-2-methanol and, more particularly, to a process for producing, from an optically active 4-oxo-2-azetidinecarboxylic acid derivative, an optically active azetidine-2-methanol and an optically active carboxylic acid each corresponding to it.

Among the optical active azetidine-2-carboxylic acids, (S)-azetidine-2-carboxylic acid is a compound useful as an intermediate for the production of medicinals. In particular, it is a compound very useful as an intermediate for the production of a thrombin inhibitor described in International Patent Applications WO 93/06069 and WO 93/11152, among others.

BACKGROUND ART

The so-far known processes for producing (S)-azetidine-2-carboxylic acid are as follows: (1) The process which comprises reacting L-2,4-diaminobutyric acid with hydrochloric acid and nitrous acid to give L-2-chloro-4-aminobutyric acid and then subjecting the same to heat treatment in barium hydroxide to give L-azetidine-2-carboxylic acid (The Biochemical Journal, vol. 64, pp. 323 to 332, 1956); (2) The process which comprises reacting-γ-butyrolactone with bromine in the presence of red phosphorus and treating the reaction product with benzyl alcohol saturated with hydrogen chloride gas to give benzyl DL-2,4-dibromobutyrate, reacting the same with benzhydrylamine to give benzyl DL-N-diphenylmethylazetidine-2-carboxylate, reducing this with hydrogen in methanol in the presence of palladium carbon to give DL-azetidine-2-carboxylic acid, and then subjecting it to reacting with benzyloxycarbonyl chloride (ZCl) to give DL-N-Z-azetidine-2-carboxylic acid, subjecting the latter to optical resolution using L-thyrosine hydrazide to give L-form, namely (S)-N-Z-azetidine-2-carboxylic acid (wherein Z represents a benzyloxycarbonyl group; hereinafter the same shall apply), and lastly reducing the same again with hydrogen in methanol in the presence of palladium carbon to give L-azetidine-2-carboxylic acid (Journal of Heterocyclic Chemistry, vol. 6, pp. 435 to 437, pp. 993 to 994, 1969); and (3) The process which comprises S-alkylating L-N-tosyl-methionine to give L-N-tosyl-methioninesulfonium salt, heating it in an aqueous solution of sodium hydroxide for conversion to L-N-tosyl-α-amino-γ-butyrolactone, treating the latter with a gaseous hydrogen halide in an alcohol to give alkyl L-N-tosyl-2-amino-4-halobutyrate, treating this with sodium hydride in dimethylformamide to give (S)-N-tosyl-azetidine-2-carboxylic acid, and thereby effecting the cyclization reaction, and detosylating it with metallic sodium in liquid ammonia to give (S)-azetidine-2-carboxylic acid (Japanese Patent Application sho-49-14457, Chemistry Letters, pp. 5 to 6, 1973).

SUMMARY OF THE INVENTION

However, the above processes each has its problems, as follows.

In process (1), L-2,4-diaminobutyric acid is expensive and, in addition, it is necessary to carry out the reaction procedure in step 1 in a more strict manner, since its reaction temperature and reaction time influence the optical purity of the desired product.

In process (2), multiple steps are required and, in addition, benzhydrylamine is expensive and the unnecessary optical isomer produced by optical resolution must be discarded unless an advantageous method of racemization is discovered, hence the process is uneconomical.

In process (3), multiple steps are required and, in addition, a low-temperature apparatus is required and care should be taken in handling in the detosylation step since, in that step, metallic sodium is used in liquid ammonia. Further, an ion exchange resin is required in the last purification step for separating the desired product from the inorganic ion, hence the productivity is low.

Thus, when viewed as an industrial production process, every prior art process has problems to be solved.

In view of the above-mentioned state of the art, the present invention has for its object to provide a process for producing azetidine-2-carboxylic acid and an intermediate thereof, which is efficient and economical and suited for industrial practice.

The present invention is related to a process for producing azetidine-2-carboxylic acid of the following formula (5)

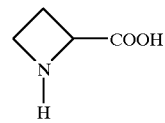

(5)

which comprises subjecting a 4-oxo-2-azetidinecarboxylic acid derivative represented by the general formula (1):

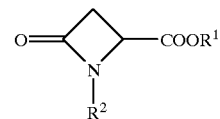

(1)

[in the formula, $R^1$ represents a hydrogen atom, an alkyl group containing 1 to 30 carbon atoms, an aryl group containing 6 to 35 carbon atoms, an aralkyl group containing 7 to 36 carbon atoms or a silyl group of the formula

$SiR^3R^4R^5$ (in the formula, $R^3$, $R^4$ and $R^5$ are the same or different, and each represents an alkyl group containing 1 to 30 carbon atoms, an aryl group containing 6 to 35 carbon atoms or an aralkyl group containing 7 to 36 carbon atoms). $R^2$ represents a hydrogen atom or a silyl group of the formula

$SiR^6R^7R^8$ (in the formula, $R^6$, $R^7$ and $R^8$ are the same or different, and each represents an alkyl group containing 1 to 30 carbon atoms, an aryl group containing 6 to 35 carbon atoms or an aralkyl group containing 7 to 36 carbon atoms)] to hydride reduction to give azetidine-2-methanol of the following formula (2):

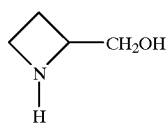

treating the same with an amino-protecting agent to give an N-protected azetidine-2-methanol represented by the following general formula (3):

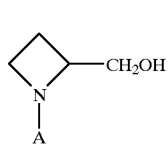

(in the formula, A represents an amino-protecting group), treating this with an oxidizing agent to give an N-protected azetidine-2-carboxylic acid represented by the following general formula (4):

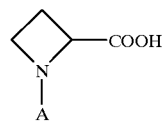

(in the formula, A is as defined above), and, further, subjecting the amino-protecting group thereof to elimination.

The present inventors made investigations in search for an efficient and economical process for commercially producing azetidine-2-carboxylic acid and, as a result, found that when a 4-oxo-2-azetidinecarboxylic acid derivative, which can be readily produced from aspartic acid which is inexpensive, is treated with a hydride reducing agent, azetidine-2-methanol can be produced as a result of simultaneous reduction of the ester group and amide group or the carboxylic acid moiety and amide group, that an N-protected azetidine-2-carboxylic acid can be produced by treating the resulting azetidine-2-methanol with an amino-protecting agent to give an N-protected azetidine-2-methanol, followed by treating the same with an oxidizing agent and, further, that azetidine-2-carboxylic acid can be produced by subjecting the thus-obtained N-protected azetidine-2-carboxylic acid to protective group elimination. Based on these findings, the present invention has now been completed.

DETAILED DISCLOSURE OF THE INVENTION

Figure 1:
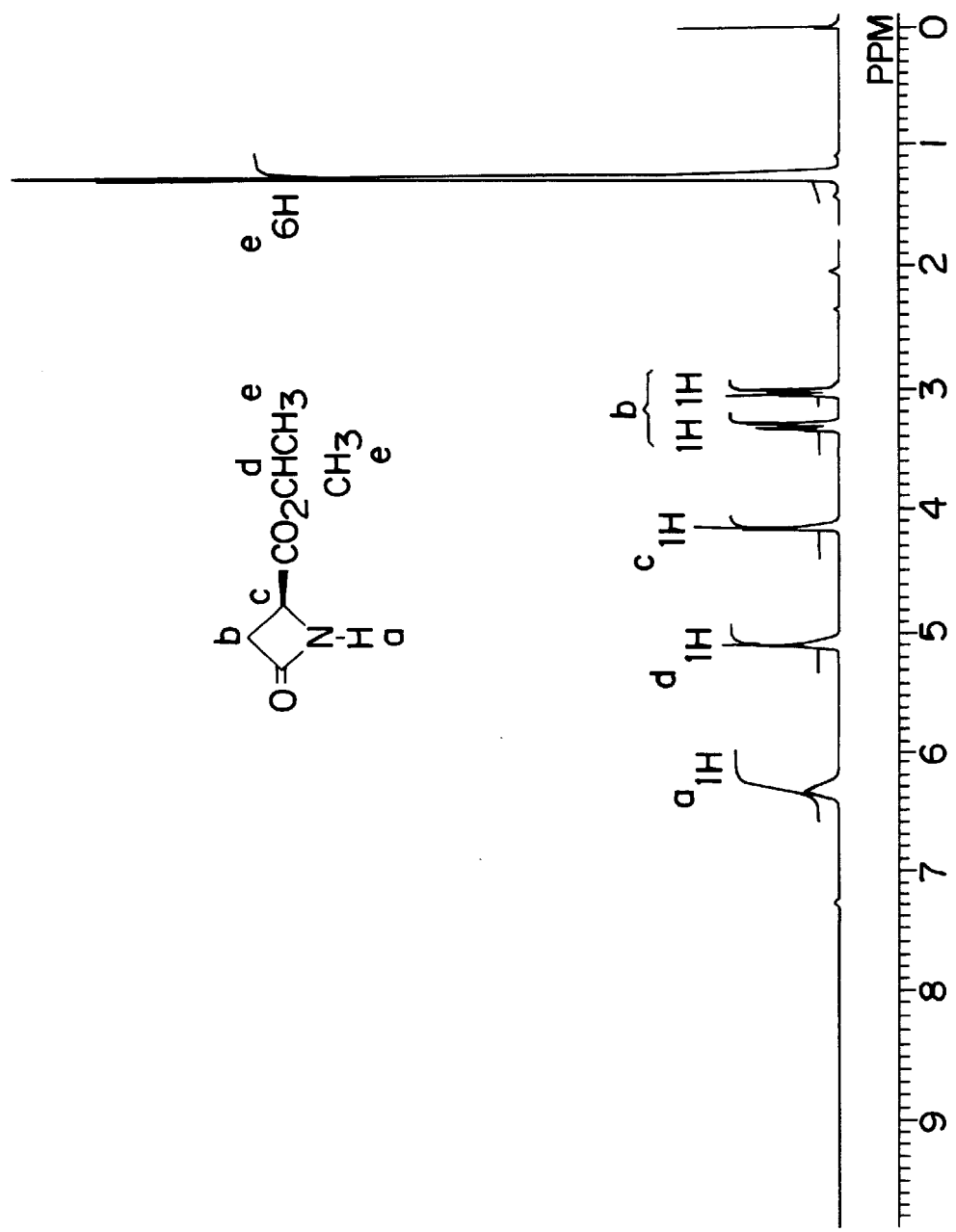
FIG. 1 is a proton NMR spectrum (solvent: $CDCl_3$) of the isopropyl (2S)-4-oxo-2-azetidinecarboxylate obtained in Reference Example 2.

In the following, the present invention is described in detail.

The process for producing azetidine-2-carboxylic acid and intermediates thereof is outlined below in terms of reaction scheme.

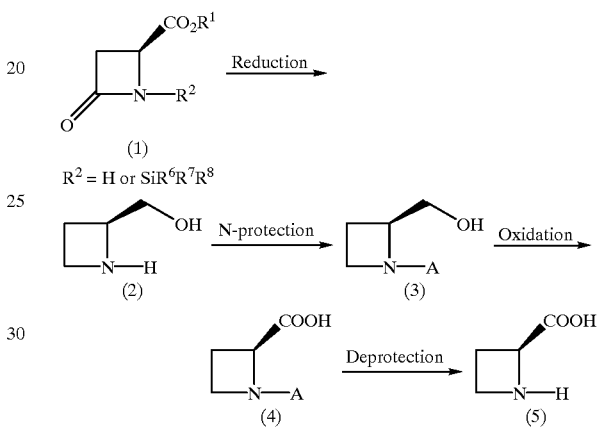

According to the present invention, azetidine-2-methanol of the above formula (2) is first produced by reducing the 4-oxo-2-azetidinecarboxylic acid derivative represented by the above general formula (1).

In the above general formula (1), $R^1$ represents a hydrogen atom, an alkyl group containing 1 to 30 carbon atoms, an aryl group containing 6 to 35 carbon atoms, an aralkyl group containing 7 to 36 carbon atoms or a silyl group represented by the formula $SiR^3R^4R^5$.

In the formula, $R^3$, $R^4$ and $R^5$ are the same or different, and each represents an alkyl group containing 1 to 30 carbon atoms, an aryl group containing 6 to 35 carbon atoms or an aralkyl group containing 7 to 36 carbon atoms. $R^2$ represents a hydrogen atom or a silyl group of the formula $SiR^6R^7R^8$.

In the formula, $R^6$, $R^7$ and $R^8$ are the same or different, and each represents an alkyl group containing 1 to 30 carbon atoms, an aryl group containing 6 to 35 carbon atoms or an aralkyl group containing 7 to 36 carbon atoms. These groups each may be straight or branched. Such are not particularly restricted but may be, for example, methyl, ethyl, n-propyl, isopropyl, n-butyl, isobutyl, t-butyl, phenyl, benzyl, (α-methylbenzyl, phenylpropyl, trimethylsilyl, triethylsilyl, t-butyldimethylsilyl, etc. Preferred among these are methyl, ethyl, n-propyl, isopropyl, n-butyl, isobutyl, t-butyl, trimethylsilyl, triethylsilyl, and t-butyldimethylsilyl. The above $R^1$ may partly be substituted by one or more substituents. Said substituents are not particularly restricted, but there may be mentioned, for example, halogens, nitro, hydroxy, an ether group, an amide group and the like.

When, in the above general formula (1), $R^2$ is a silyl group represented by the formula $$SiR^6R^7R^8.$$

Said silyl group is not particularly restricted but may be, for example, trimethylsilyl, triethylsilyl, t-butyldimethylsilyl or the like. Preferred among these are trimethylsilyl and triethylsilyl.

The 4-oxo-2-azetidinecarboxylic acid derivative represented by the above general formula (1) can be produced, for example, by the process described in the detailed description in the specification of U.S. Pat. No. 4,174,316 or European Patent No. 7973, for instance. More specifically, it can be produced in the following manner.

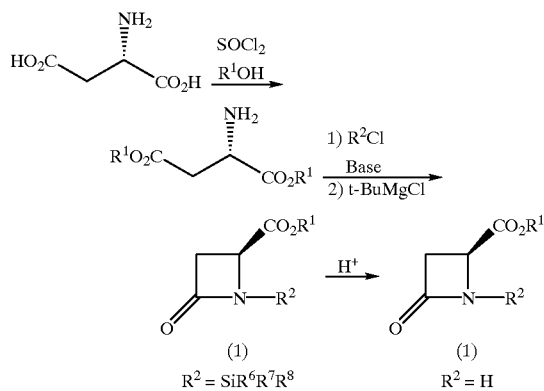

4-oxo-2-azetidinecarboxylic acid derivatives represented by the general formula (1) in which $R^2$ is a silyl group can be prepared by treating aspartic acid with, for example, thionyl chloride in an alcohol to give aspartic acid diester hydrochloride, then protecting the nitrogen atom thereof with a silylating agent, such as trimethylsilyl chloride, in a solvent, such as toluene, in the presence of a base, such as triethylamine and treating the thus-protected intermediate with a Grignard reagent, such as t-butylmagnesium chloride. 4-oxo-2-azetidinecarboxylic acid derivatives represented by the general formula (1) in which $R^2$ is a hydrogen atom can be obtained by further treatment of the same with an acid, for instance.

The step of producing azetidine-2-methanol of the general formula (2) in which said 4-oxo-2-azetidinecarboxylic acid derivative of the general formula (1) is reduced with a hydride is now described in the following.

The reducing agent to be used in the hydride reduction of the 4-oxo-2-azetidinecarboxylic acid derivative of the above general formula (1) is not particularly restricted but includes, among others, aluminum hydride-based reducing agents, boron hydride-based reducing agents and the like. As specific examples, there may be mentioned, among others, diisobutyl-aluminum hydride, sodium bis(methoxyethoxy) aluminum hydride, lithium aluminum hydride, lithium aluminum hydride-aluminum chloride, borane, sodium borohydride-methyl iodide and the like. The use of lithium aluminum hydride, among others, is preferred.

The optimal amount of said reducing agents may vary depending on the reducing agent employed. In the case of lithium aluminum hydride, for instance, it is used preferably in an amount of 1 to 6 equivalent moles, more preferably 1.2 to 5 equivalent moles, relative to the 4-oxo-2-azetidinecarboxylic acid derivative of the above general formula (1).

The reaction solvent to be used in reducing the 4-oxo-2-azetidinecarboxylic acid derivative of the above general formula (1) is not particularly restricted unless the reduction reaction is adversely affected, but includes, among others, ether type solvents, aromatic hydrocarbon type solvents and the like. As specific examples, there may be mentioned tetrahydrofuran, t-butyl methyl ether, diethyl ether, 1,2-dimethoxyethane and toluene, among others. These may be used either singly or combinedly as a mixed solvent composed of two or more of them.

For the hydride reduction of the 4-oxo-2-azetidinecarboxylic acid derivative of the above general formula (1), a solution of said 4-oxo-2-azetidinecarboxylic acid derivative of the above general formula (1) is first added to a solution of the reducing agent mentioned above which is preferably maintained at −70 to 110° C., more preferably −50 to 100° C., most preferably −30 to 65° C., and the mixture is stirred preferably for 30 minutes to 20 hours, more preferably 1 to 10 hours. In this step, said reducing agent or a solution thereof may be added to a solution of the 4-oxo-2-azetidinecarboxylic acid derivative of the above general formula (1), which is to be followed by stirring under the same conditions as mentioned above.

In carrying out the hydride reduction of the 4-oxo-2-azetidinecarboxylic acid derivative of the above general formula (1), by treating said 4-oxo-2-azetidinecarboxylic acid derivative with the hydride reducing agent after addition of a Grignard agent and/or a magnesium salt, azetidine-2-methanol of the above general formula (2) can be obtained in high yields while preventing formation of the byproduct 2-amino-1,4-butanediol.

When the hydride reduction of said 4-oxo-2-azetidinecarboxylic acid derivative of the above general formula (1) is carried out in the presence of a Grignard reagent, said Grignard reagent is used preferably in an amount of 0.5 to 2.0 equivalent moles, more preferably 1.0 to 1.1 equivalent moles, relative to the 4-oxo-2-azetidinecarboxylic acid derivative of the above general formula (1).

Among them, said Grignard reagent is not particularly restricted but includes, t-butylmagnesium chloride, ethylmagnesium chloride, methylmagnesium chloride and the like. Among them, t-Butylmagnesium chloride is suited for use.

Said magnesium salt is not particularly restricted but includes, among others, magnesium chloride, magnesium bromide, magnesium iodide, magnesium fluoride, magnesium sulfate and the like. Among them, magnesium chloride is preferred.

When the hydride reduction mentioned above is carried out in the presence of magnesium chloride, said magnesium chloride is used preferably in an amount of 0.5 to 2.0 equivalent moles, more preferably 1.0 to 1.7 equivalent moles, relative to the 4-oxo-2-azetidinecarboxylic acid derivative of the above general formula (1).

As regards the reaction procedure in those cases where the hydride reduction of the 4-oxo-2-azetidinecarboxylic acid derivative of the above general formula (1) is carried out in the presence of a Grignard agent and magnesium salt, said Grignard reagent is added to a solution of said 4-oxo-2-azetidinecarboxylic acid derivative of the above general formula (1) and said magnesium salt, for example, in the reaction solvent mentioned above, preferably at −70 to 50° C., more preferably −50 to 40° C., still more preferably −30 to 30° C., and the mixture is stirred for 30 minutes to 3 hours, preferably 1 to 2 hours. The thus-obtained solution is added to a solution of the above-mentioned reducing agent, preferably at −70 to 110° C., more preferably −50 to 100° C., still more preferably −30 to 65° C., and the mixture is stirred for the same period as mentioned above. In this case, a solution of the reducing agent may be added to a solution of said 4-oxo-2-azetidinecarboxylic acid derivative, followed by stirring under the same conditions as mentioned above. Said magnesium salt may be used in the form of a mixture with said reducing agent.

Then, after the lapse of the above reaction time, the reaction is quenched by adding water, diluted hydrochloric acid, aqueous ammonium chloride or the like. Further, the pH of the thus-treated mixture is adjusted preferably to pH 7 to 9, more preferably 7 to 8, by adding concentrated hydrochloric acid or the like and the mixture is subjected to column chromatography or like general processing procedure, whereby azetidine-2-methanol of the above formula (2) can be separated, although it is preferred that this azetidine-2-methanol be used in the next step without separation/purification.

The addition of a Grignard reagent and a magnesium salt, as mentioned above, according to the present invention is supposed to lead to formation of a lactam N-magnesium salt, and this is presumably the cause of an increased yield in the reduction step.

In the step of hydride reduction of a 4-oxo-2-azetidinecarboxylic acid derivative represented by the general formula (1) in which $R^2$ is a silyl group as mentioned above, the desired product, namely azetidine-2-methanol of the above general formula (2), can be obtained in higher yields while preventing the formation of the byproduct 2-amino-1,4-butanediol, by carrying out the reduction after preliminary treatment with the magnesium salt, a quaternary ammonium halide and a fluoride salt, although the treatment with the hydride reducing agent may be carried out with addition of the Grignard reagent and/or magnesium salt.

In that case, said magnesium salt is used preferably in an amount of 1.0 to 3.0 equivalent moles, more preferably 1.5 to 2.5 equivalent moles, relative to the 4-oxo-2-azetidinecarboxylic acid derivative of the above general formula (1). Said quaternary ammonium halide is used preferably in an amount of 0.005 to 1.0 equivalent mole, more preferably 0.1 to 0.5 equivalent mole, relative to the 4-oxo-2-azetidinecarboxylic acid derivative of the above general formula (1). Said fluoride salt is used preferably in an amount of 0.5 to 2.0 equivalent moles, more preferably 1.0 to 1.1 equivalent moles, relative to the 4-oxo-2-azetidinecarboxylic acid derivative of the above general formula (1).

Said quaternary ammonium halide is not particularly restricted but includes, among others, tetrabutylammonium fluoride (TBAF), tetrabutylammonium chloride, tetrabutylammonium bromide and the like. Among them, TBAF is preferred.

Said fluoride salt is not particularly restricted but includes, among others, potassium fluoride, sodium fluoride, magnesium fluoride and the like. Among them, potassium fluoride and magnesium fluoride are preferred.

As for the reaction conditions in the step of hydride reduction of the 4-oxo-2-azetidinecarboxylic acid derivative of the general formula (1) in which $R^2$ is a silyl group as mentioned above following treatment thereof with magnesium fluoride in the presence of magnesium chloride and TBAF, TBAF is added, for example, to a solution of the 4-oxo-2-azetidinecarboxylic acid derivative of the general formula (1) in which $R^2$ is the silyl group as mentioned above, magnesium chloride and magnesium fluoride in a solvent as mentioned above, preferably at −70 to 50° C., more preferably −50 to 40° C., still more preferably −30 to 30° C., and the mixture is stirred preferably for 30 minutes to 3 hours, more preferably 1 to 2 hours. The solution resulting from the above treatment of the 4-oxo-2-azetidinecarboxylic acid derivative is added to a solution of the above reducing agent, preferably at −70 to 110° C., more preferably −50 to 100° C., still more preferably −30 to 65° C., and the mixture is stirred for the same period as mentioned above. In this case, it is also possible to add the solution of the above reducing agent to a solution of the 4-oxo-2-azetidinecarboxylic acid derivative treated as mentioned above and then stir the mixture under the same conditions as mentioned above.

After the lapse of the above reaction time, the reaction is quenched by adding water, diluted hydrochloric acid, aqueous ammonium chloride or the like. Further, the pH of the thus-treated mixture is adjusted preferably to pH 7 to 9, more preferably 7 to 8, by adding concentrated hydrochloric acid or the like and the mixture is subjected to column chromatography or like per se known general processing procedure, whereby azetidine-2-methanol of the general formula (2) can be separated, although it is preferred that this reduction reaction mixture be used in the next protecting step without separation/purification.

According to the present invention, said azetidine-2-methanol of the above general formula (2) is then treated with an amino-protecting agent to give an N-protected azetidine-2-methanol represented by the above general formula (3).

In the above general formula (3), A represents an amino-protecting group. Said amino-protecting group is not particularly restricted but may be any group capable of protecting the amino group in the oxidation reaction step. Thus, said protective group includes, among others, alkoxycarbonyl type protective groups represented by the general formula:

—COOR⁹

(in the formula, $R^9$ represents an alkyl group containing 1 to 30 carbon atoms, an aryl group containing 6 to 35 carbon atoms or an aralkyl group containing 7 to 36 carbon atoms), acyl type protective groups represented by the general formula:

—COR⁹

(in the formula, $R^9$ is as defined above), protective groups represented by the general formula:

—CHR¹⁰R¹¹

(in the formula, $R^{10}$ represents a hydrogen atom or an aryl group containing 6 to 35 carbon atoms. $R^{11}$ represents an aryl group containing 6 to 35 carbon atoms), and sulfonyl type protective groups represented by the general formula:

—SOOR⁹

(in the formula, $R^9$ is as defined above).

As specific examples, there may be mentioned, among others, methoxycarbonyl, ethoxycarbonyl, t-butoxycarbonyl, benzyloxycarbonyl, acetyl, trifluoroacetyl, benzoyl, benzyl, p-toluenesulfonyl and methanesulfonyl. Among these, methoxycarbonyl, ethoxycarbonyl, t-butoxycarbonyl, benzyloxycarbonyl, benzyl and the like are preferred because of ease of elimination procedure.

Said amino-protecting agent for the amino protecting group introduction mentioned above is not particularly restricted but includes, among others, chlorocarbonate ester type protecting agents represented by the general formula:

(in the formula, $R^9$ is as defined above), dicarbonate ester type protecting agents represented by the general formula:

(in the formula, $R^9$ is as defined above), acyl chloride type protecting agents represented by the general formula:

(in the formula, $R^9$ is as defined above), protecting agents represented by the general formula:

(in the formula, $R^{10}$ and $R^{11}$ are as defined above. X represents a halogen atom), and sulfonyl chloride type protecting agents represented by the general formula:

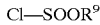

(in the formula, $R^9$ is as defined above).

As specific examples, there may be mentioned, among others, methyl chlorocarbonate, ethyl chlorocarbonate, di-t-butyl dicarbonate, benzyloxycarbonyl chloride, acetyl chloride, trifluoroacetyl chloride, benzoyl chloride, benzyl chloride, p-toluenesulfonyl chloride, methanesulfonyl chloride and the like. Among these, methyl chlorocarbonate, ethyl chlorocarbonate, di-t-butyl dicarbonate, benzyloxycarbonyl chloride, trifluoroacetyl chloride and benzyl chloride are judiciously used.

Said amino-protecting agent is used preferably in an amount of 1 to 3 equivalent moles relative to azetidine-2-methanol of the above formula (2). More preferably 1 to 1.5 equivalent moles.

As a reaction solvent used for treating with said amino-protecting agent and without separation/purification, when a chlorocarbonate ester protecting agent, an acyl chloride type protecting agent or di-t-butyl dicarbonate is used as said amino-protecting agent, there can be used, for example, a two-layer solvent composed of toluene, ethyl acetate, tetrahydrofuran or the like single solvent or a mixture of these, and water.

In the case of sulfonyl chloride type protecting agents, toluene, ethyl acetate, tetrahydrofuran or the like single solvent or a mixture of these is used.

Prior to treatment with said amino-protecting agent, a base is preferably added to the solvent. Said base is not particularly restricted but may be, for example, sodium carbonate, sodium hydrogen carbonate, sodium hydroxide, potassium hydroxide or the like. It is used preferably in an amount of 1 to 2 equivalent moles, more preferably 1 to 1.5 equivalent moles, relative to the amino-protecting agent.

For obtaining the N-protected azetidine-2-methanol of the above general formula (3) by treating azetidine-2-methanol of the above formula (2) with said amino-protecting agent, a solution of azetidine-2-methanol of the above formula (2) and the amino-protecting agent in a reaction solvent as mentioned above is first stirred preferably at 0 to 100° C., more preferably 10 to 70° C., preferably for 1 to 20 hours, more preferably 2 to 10 hours.

Then, after the lapse of said reaction period, the reaction is quenched by adding diluted hydrochloric acid, aqueous ammonium chloride or the like. The product is extracted with a solvent such as ethyl acetate, diethyl ether or toluene and the extract is washed with a saturated aqueous solution of sodium hydrogen carbonate, a saturated aqueous solution of sodium chloride and/or the like, dried over a drying agent such as sodium sulfate or magnesium sulfate and, after filtering off the drying agent and concentration, treated by such an ordinary procedure as recrystallization, column chromatography or the like, whereby the N-protected azetidine-2-methanol of the above general formula (3) can be isolated. It is also possible to use the N-protected azetidine-2-methanol obtained in the above manner in the next step without separation/purification.

According to the present invention, the N-protected azetidine-2-methanol of the above general formula (3) is then treated with an oxidizing agent to give the N-protected azetidine-2-carboxylic acid of the above general formula (4).

Said oxidizing agent is not particularly restricted but there may be mentioned, for example, manganese dioxide, chromium trioxide, 2,2,6,6-tetramethylpiperidine-1-oxyl (TEMPO)/sodium hypochlorite/bromide salt, 4-hydroxy-TEMPO/sodium hypochlorite/bromide salt, and the like. Among these, TEMPO/sodium hypochlorite/bromide salt and 4-hydroxy-TEMPO/sodium hypochlorite/bromide salt are judiciously used.

In this case, said TEMPO or 4-hydroxy-TEMPO is used preferably in an amount of 0.01 to 0.5 equivalent mole, more preferably 0.01 to 0.02 equivalent mole, relative to the N-protected azetidine-2-methanol of the above general formula (3). Said sodium hypochlorite is used preferably in an amount of 2 to 5 equivalent moles, more preferably 2 to 4 equivalent moles, relative to the N-protected azetidine-2-methanol of the above general formula (3). Said bromide salt is, for example, sodium bromide or potassium bromide, and it is used preferably in an amount of 0.1 to 0.5 equivalent mole, more preferably 0.1 to 0.2 equivalent mole, relative to the N-protected azetidine-2-methanol of the above general formula (3).

The reaction solvent to be used in treating the N-protected azetidine-2-methanol of the above general formula (3) with said oxidizing agent is not particularly restricted but may be, for example, a two-layer solvent composed of toluene, ethyl acetate, tetrahydrofuran or a like single solvent or a mixture of these, and water.

For obtaining the N-protected azetidine-2-carboxylic acid of the above general formula (4) by treating the N-protected azetidine-2-methanol of the above general formula (3) with said oxidizing agent, for example the above-mentioned TEMPO/sodium hypochlorite/bromide salt system, an aqueous solution of sodium hypochlorite is first added to a mixture of the N-protected azetidine-2-methanol of the above general formula (3), TEMPO and the bromide salt in a solvent as mentioned above, preferably at 0 to 50° C., more preferably 0 to 10° C., and the resulting mixture is stirred preferably for 1 to 5 hours, more preferably 1 to 2 hours.

Then, after the lapse of the above reaction time, the reaction is quenched by decomposing the excess sodium hypochlorite by adding sodium thiosulfate, the aqueous layer is adjusted to pH 1 to 3 with an acid such as concentrated hydrochloric acid and extracted with a solvent such as ethyl acetate, diethyl ether or toluene, and the extract is washed with a saturated aqueous solution of sodium chloride and/or the like, dried over a drying agent such as sodium sulfate or magnesium sulfate and, and, after filtering off the drying agent and concentration, treated by such an ordinary procedure as recrystallization, column chromatography or the like, whereby the N-protected azetidine-2- carboxylic acid of the above general formula (4) can be isolated. It is also possible to use the N-protected azetidine-2-carboxylic acid obtained in the above manner in the next step without separation/purification.

The N-protected azetidine-2-carboxylic acid of the above general formula (4) may be directly submitted, without elimination of said amino-protecting group, to a process for producing the thrombin inhibitor mentioned above. In this case, said amino-protecting group as it is can function as a protective group in the amide formation reaction and generally in the oxidation reaction.

According to the present invention, the azetidine-2-carboxylic acid of the above general formula (5) can be produced by eliminating the amino-protecting group from the N-protected azetidine-2-carboxylic acid of the above general formula (4).

For eliminating the amino-protecting group from the N-protected azetidine-2-carboxylic acid of the above general formula (4), general methods such as those described, for example, in Theodora W. Green: Protective Groups in Organic Synthesis, second edition, John Wiley & Sons, 1990 can be employed.

Specifically, when, for example, the amino-protecting group in the N-protected azetidine-2-carboxylic acid of the above general formula (4) is benzyloxycarbonyl, the benzyloxycarbonyl group can be eliminated by treating said N-protected azetidine-2-carboxylic acid of the above general formula (4) in a solvent, such as methanol, in a hydrogen atmosphere in the presence of a catalyst such as palladium carbon.

After the thus-effected amino-protecting group elimination, the palladium carbon is filtered off and washed with water, the filtrate and washings are combined and concentrated and subjected to a general procedure such as recrystallization, whereby the desired product azetidine-2-carboxylic acid of the above formula (5) can be isolated and purified.

In the process of the present invention for producing azetidine-2-carboxylic acid and intermediates thereof, when an optically active 4-oxo-2-azetidinecarboxylic acid derivative is used, each production step mentioned above can be conducted substantially without causing racemization. Therefore, by using an (S)-4-oxo-2-azetidinecarboxylic acid derivative produced from optically active L-aspartic acid as the above-mentioned 4-oxo-2-azetidinecarboxylic acid derivative of the above general formula (1), it is possible to produce (S)-azetidine-2-methanol, an (S)-N-protected azetidine-2-methanol, an (S)-N-protected azetidine-2-carboxylic acid, and (S)-azetidine-2-carboxylic acid.

BEST MODES FOR CARRYING OUT THE INVENTION

The following examples illustrate the present invention in further detail. These examples are, however, by no means limitative of the scope of the present invention.

REFERENCE EXAMPLE 1

Synthesis of Diisopropyl L-aspartate Hydrochloride

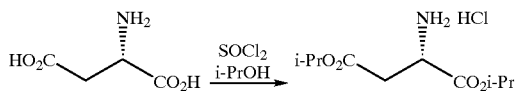

In a reaction flask equipped with a condenser and a mechanical stirrer, L-aspartic acid (133.1 g, 1.00 mol) was dispersed in isopropanol (700 mL). While slowly adding thionyl chloride (500 mL, 6.84 mol) thereto, the solution temperature was raised to the refluxing temperature of the contents and, after completion of the addition, the mixture was heated under reflux with stirring for 7 hours. Then, the reaction mixture was concentrated to a volume about one fourth of the initial volume by vacuum distillation. To the concentrate was added methyl t-butyl ether (800 mL) with stirring to cause crystallization. The resulting crystals were collected by filtration, washed with methyl t-butyl ether (300 mL) and dried under reduced pressure to give diisopropyl L-aspartate hydrochloride as white crystals (209.8 g, yield 92.0%).

REFERENCE EXAMPLE 2

Synthesis of Isopropyl (2S)-4-oxo-2-azetidinecarboxylate

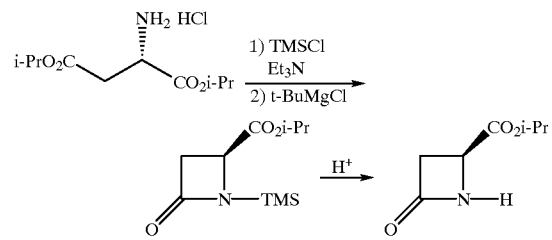

In a reaction flask equipped with a mechanical stirrer, the diisopropyl L-aspartate hydrochloride (76.2 g, 0.300 mol) obtained in Reference Example 1 was added to toluene (400 mL) and trimethylsilyl chloride (32.7 g, 0.300 mol) in a nitrogen gas atmosphere, followed by addition of triethylamine (63.8 g, 0.630 mol) at 5 to 10° C. Thereafter, the solution temperature was raised to room temperature and stirring was further continued for an hour. The resulting white precipitate was filtered off and washed with toluene (200 mL). The filtrate and washings were combined in a separate reaction flask and, to this toluene solution, t-butylmagnesium chloride (2 M solution in THF, 180 mL, 0.36 mol) was added in a nitrogen gas atmosphere at 5 to 10° C. and, then, the reaction was allowed to proceed for 3 hours while raising the solution temperature to 30° C. Then, at 5° C., the reaction mixture was adjusted to pH 1 by adding 10% sulfuric acid (200 mL). After phase separation, the organic layer was separated, washed with a saturated aqueous solution of sodium hydrogen carbonate (100 mL×1) and then with a saturated aqueous solution of sodium chloride (100 mL×1), dried over magnesium sulfate and filtered, and the filtrate was concentrated. The concentrate was subjected to separation/purification by column chromatography (Wakogel C-200) using toluene/ethyl acetate (1/1) as a mobile phase, to give a pale yellow oil (29.2 g). This was identified, based on its proton NMR spectrum (FIG. 1), as the desired isopropyl (2S)-4-oxo-2-azetidinecarboxylate (yield 62.0%).

REFERENCE EXAMPLE 3

Synthesis of Isopropyl (2S)-4-oxo-1-trimethylsilyl-2-azetidinecarboxylate

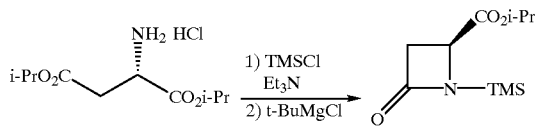

Figure 2:
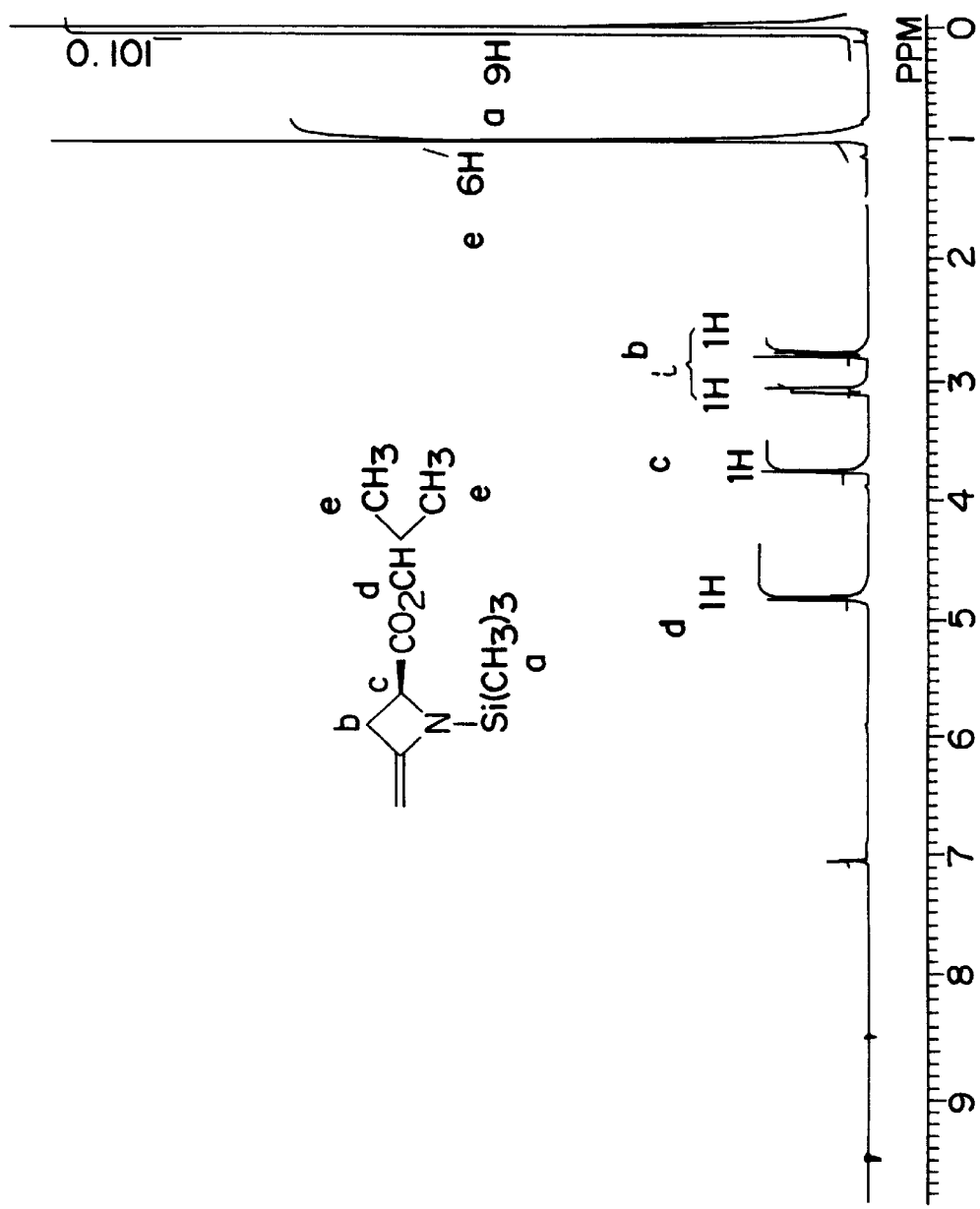
FIG. 2 is a proton NMR spectrum (solvent: $CDCl_3$) of the isopropyl (2S)-4-oxo-1-trimethylsilyl-2-azetidinecarboxylate obtained in Reference Example 3.

In a reaction flask equipped with a mechanical stirrer, the diisopropyl L-aspartate hydrochloride (33.9 g, 0.134 mol) obtained in Reference Example 1 was added to toluene (200 mL) and trimethylsilyl chloride (16.0 g, 0.147 mol) in a nitrogen gas atmosphere, followed by addition of triethylamine (28.47 g, 0.281 mol) at 5 to 10° C. Thereafter, the solution temperature was raised to room temperature and stirring was further continued for 2.5 hours. The resulting white precipitate was filtered off and washed with toluene (100 mL). The filtrate and washings were combined in a separate reaction flask and, to this toluene solution, t-butylmagnesium chloride (2 M solution in THF, 73.5 mL, 0.147 mol) was added in a nitrogen gas atmosphere at 5 to 10° C. and, then, the reaction was allowed to proceed for 3 hours while raising the solution temperature to 30° C. Then, at 5° C., the reaction mixture was adjusted to pH 2 by adding 1 M citic acid (200 mL). After phase separation, the organic layer was recovered, washed with a saturated aqueous solution of sodium hydrogen carbonate (100 mL×1) and then with a saturated aqueous solution of sodium chloride (100 mL×1), dried over magnesium sulfate and filtered, and the filtrate was concentrated to give a pale yellow oil (21.0 g). This was identified, based on its proton NMR spectrum (FIG. 2), as the desired isopropyl (2S)-4-oxo-1-trimethylsilyl-2-azetidinecarboxylate (yield 68.0%).

EXAMPLE 1

Synthesis of (S)-N-benzyloxycarbonylazetidine-2-methanol

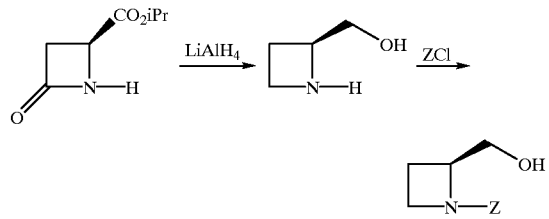

In a nitrogen gas atmosphere, a reaction flask was charged with lithium aluminum hydride (0.569 g, 15.0 mmol) and THF (10 mL) and, while maintaining the temperature of the mixture at 5 to 15° C., a solution of the isopropyl (2S)-4-oxo-2-azetidinecarboxylate (1.57 g, 10.0 mmol) obtained in Reference Example 2 in THF (5 mL) was added. Then, the whole mixture was heated and stirred under reflux for 6 hours. This reaction mixture was cooled to 5° C., water (30 mL) was added, and the mixture was further stirred at room temperature for 0.5 hour. This solution was used as it was in the next step without isolation/purification of (S)-azetidine-2-methanol.

Figure 3:
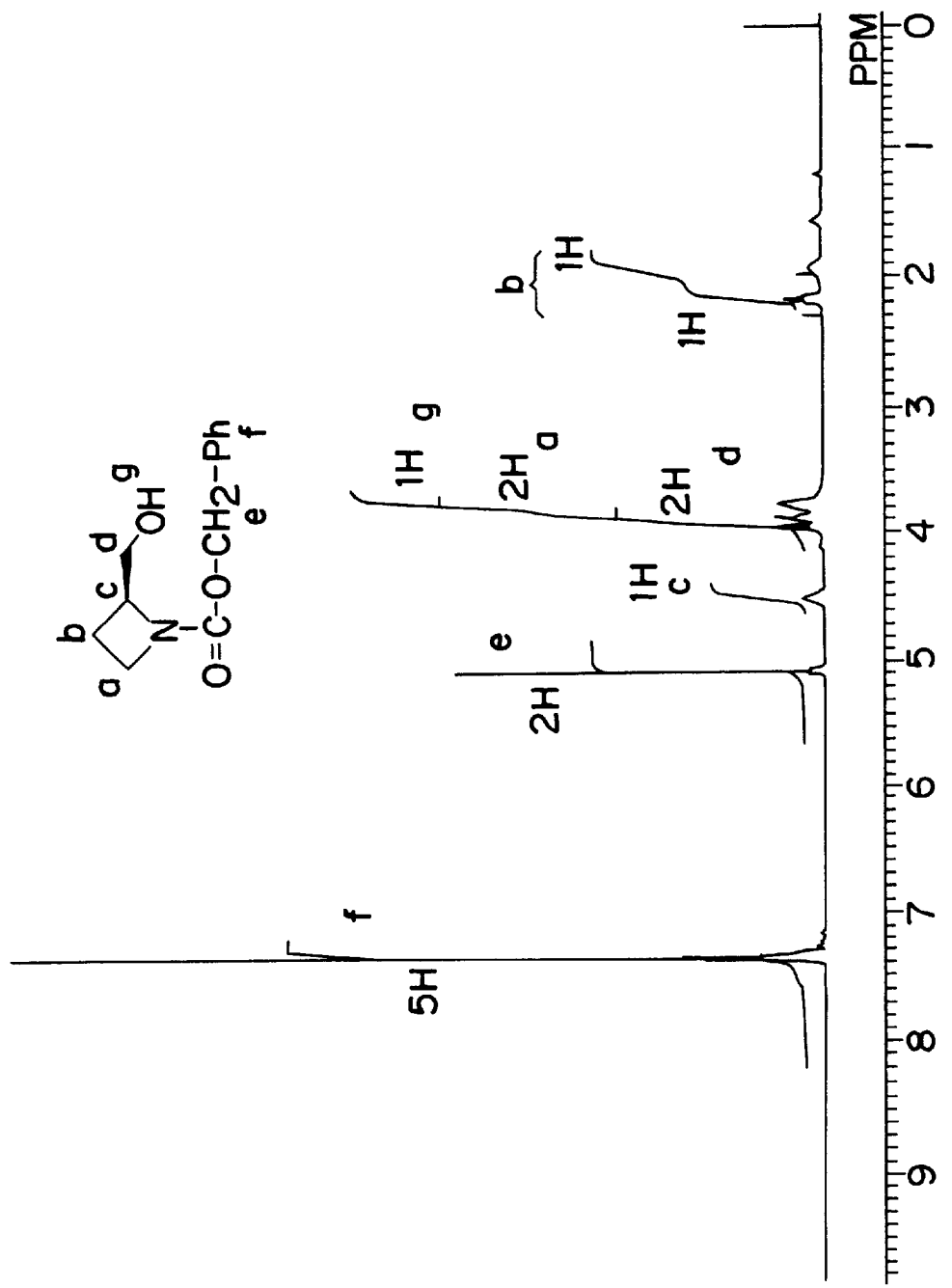
FIG. 3 is a proton NMR spectrum (solvent: $CDCl_3$) of the (S)-N-benzyloxycarbonylazetidine-2-methanol obtained in Example 1.
Figure 4:
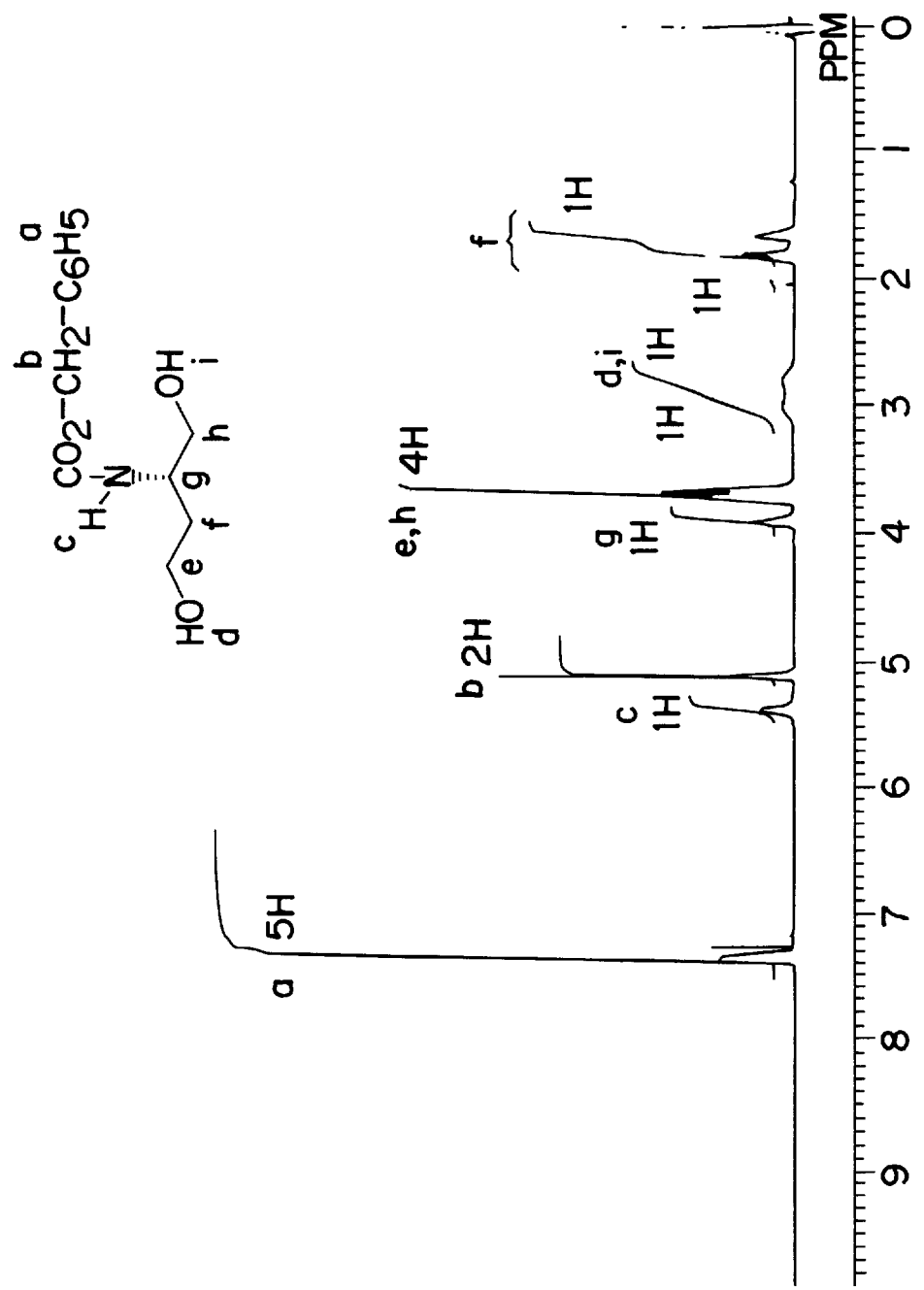
FIG. 4 is a proton NMR spectrum (solvent: $CDCl_3$) of the (S) -2-N-benzyloxycarbonyl-1,4-butanediol obtained in Example 1.

Said solution of (S)-azetidine-2-methanol was adjusted to pH 10 by adding 10% sulfuric acid, sodium hydrogen carbonate (2.00 g, 24.0 mmol) was then added and benzyloxycarbonyl chloride (ZCl) (4.00 g, 24.0mmol) was added at room temperature. Thereafter, stirring was continued for 14 hours. The mixture was adjusted to pH 7 and extracted with ethyl acetate (50 mL ×1), the extract was washed with water (50 mL×1) and dried over magnesium sulfate and, after filtering off the same, the filtrate was concentrated. This was subjected to column chromatography (Wakogel C-200) using toluene/ethyl acetate (1/1) as a mobile phase for separation and purification, whereby a pale yellow oil was obtained (1.50 g). Based on its proton NMR spectrum (FIG. 3), this was identified as the desired product (S)-N-benzyloxycarbonylazetidine-2-methanol (yield 69.1%). Further, as a byproduct, there was obtained (S)-2-N-benzyloxycarbonyl-1,4-butanediol (0.27 g, yield 11.4%). Its proton NMR spectrum is shown in FIG. 4.

EXAMPLE 2

Synthesis of (S)-N-benzyloxycarbonylazetidine-2-methanol (Effect of Addition of t-butylmagnesium Chloride)

In a nitrogen gas atmosphere, a solution of the isopropyl (2S)-4-oxo-2-azetidinecarboxylate obtained in Reference Example 2 (1.57 g, 10.0 mmol) in THF (25 mL) was prepared in a reaction flask and, while maintaining the temperature at 5 to 15° C., t-butylmagnesium chloride (2 M solution in THF, 5.00 mL, 10.0 mmol) was added, and the mixture was further stirred at that temperature for 1.5 hours.

In a nitrogen gas atmosphere, a separate reaction flask was charged with lithium aluminum hydride (0.569 g, 15.0 mmol) and THF (10 mL) and, while maintaining the temperature of the solution at 5 to 15° C., the above solution of isopropyl (2S)-4-oxo-2-azetidinecarboxylate magnesium salt in THF was added. Thereafter, the mixture was heated under reflux with stirring for 6 hours. The reaction mixture was cooled to 5° C., water (30 mL) was added and the mixture was further stirred at room temperature for 0.5 hour.

This solution of (S)-azetidine-2-methanol was adjusted to pH 10 by adding 10% sulfuric acid, sodium hydrogen carbonate (2.00 g, 24.0 mmol) was then added, and benzyloxycarbonyl chloride (4.00 g, 24.0 mmol) was added thereto at room temperature. The mixture was then stirred for 14 hours. The solution was adjusted to pH 7, and extracted with ethyl acetate (50 mL×2). The extract was washed with water (50 mL×1), dried over magnesium sulfate and filtered, and the filtrate was concentrated. The concentrate was subjected to column chromatography (Wakogel C-200) using toluene/ethyl acetate (1/1) as a mobile phase. This separation/purification gave (S)-N-benzyloxycarbonylazetidine-2-methanol (2.01 g, yield 91.0%). The yield was improved as compared with that obtained in Example 1 (69.1%). The formation of the byproduct (S)-2-N-benzyloxycarbonyl-1,4-butanediol decreased to a yield of 7.0% (0.17 g).

EXAMPLE 3

Synthesis of (S)-N-benzyloxycarbonylazetidine-2-methanol (Effect of Addition of Magnesium Chloride)

In a nitrogen gas atmosphere, a reaction flask was charged with lithium aluminum hydride (0.569 g, 15.0 mmol), magnesium chloride (1.43 g, 15.0 mmol) and THF (10 mL) and, while maintaining the temperature of this solution at 5 to 15° C., a solution of the isopropyl (2S)-4-oxo-2- azetidinecarboxylate obtained in Reference Example 2 (1.57 g, 10.0 mmol) in THF (5 mL) was added. Thereafter, the mixture was heated under ref Lux with stirring for 6 hours. The reaction mixture was cooled to 5° C., water (30 mL) was added, and the mixture was further stirred at room temperature for 0.5 hour.

This solution of (S)-azetidine-2-methanol was adjusted to pH 10 by adding 10% sulfuric acid, sodium hydrogen carbonate (2.00 g, 24.0 mmol) was then added, and benzyloxycarbonyl chloride (4.00 g, 24.0 mmol) was added thereto at room temperature. The mixture was then stirred for 14 hours. The solution was adjusted to pH 7, and extracted with ethyl acetate (50 mL×2). The extract was washed with water (50 mL×1), dried over magnesium sulfate and filtered, and the filtrate was concentrated. The concentrate was subjected to column chromatography (Wakogel C-200) using toluene/ethyl acetate (1/1) as a mobile phase. This separation/purification gave (S)-N-benzyloxycarbonylazetidine-2-methanol (1.88 g, yield 85.0%). The yield was improved as compared with that obtained in Example 1 (69.1%). The formation of the byproduct (S)-2-N-benzyloxycarbonyl-1,4-butanediol decreased to a yield of 3.0% (0.07 g).

EXAMPLE 4

Synthesis of (S)-N-benzyloxycarbonylazetidine-2-methanol (Effect of addition of t-butylmagnesium Chloride and Magnesium Chloride)

In a nitrogen gas atmosphere, a reaction flask was charged with the isopropyl (2S)-4-oxo-2-azetidinecarboxylate obtained in Reference Example 2 (1.57 g, 10.0 mmol), magnesium chloride (1.43 g, 15.0 mmol) and THF (25 mL) and, while maintaining the temperature of this solution at 515° C., t-butylmagnesium chloride (2 M solution in THF, 5.00 mL, 10 mmol) was added, followed by 1.5 hours of further stirring at that temperature.

While maintaining the temperature of that solution at 5 to 15° C., a solution of lithium aluminum hydride (0.569 g, 15.0 mmol) in THF (10 mL) was added and, thereafter, the mixture was heated under reflux with stirring for 6 hours. The reaction mixture was then cooled to 5° C., water (30 mL) was added, and the mixture was further stirred at room temperature for 0.5 hour.

This solution of (S)-azetidine-2-methanol was adjusted to pH 10 by adding 10% sulfuric acid, sodium hydrogen carbonate (2.00 g, 24.0 mmol) was then added, and benzyloxycarbonyl chloride (4.00 g, 24.0 mmol) was added at room temperature. Thereafter, stirring was continued for 14 hours. The reaction mixture was adjusted to pH 7 and extracted with ethyl acetate (50 mL×2), and the extract was washed with water (50 mL×1), dried over magnesium sulfate and filtered. The filtrate was concentrated and subjected to column chromatography (Wakogel C-200) using toluene/ethyl acetate (1/1) as a mobile phase for separation/purification, to give (S)-N-benzyloxycarbonylazetidine-2-methanol (2.14 g, yield 97.0%). The yield was improved as compared with that obtained in Example 1 (69.1%). The formation of the byproduct (S)-2-N-benzyloxycarbonyl-1,4-butanediol decreased to a yield of 2.5% (0.06 g).

EXAMPLE 5

Synthesis of (S)-N-t-butoxycarbonylazetidine-2-methanol (Effect of Addition of t-butylmagnesium Chloride and Magnesium Chloride)

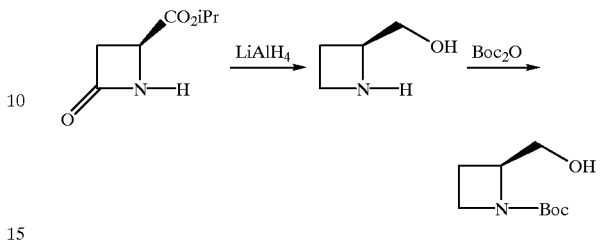

In a nitrogen gas atmosphere, a reaction flask was charged with the isopropyl (2S)-4-oxo-2-azetidinecarboxylate obtained in Reference Example 2 (5.00 g, 31.8 mmol), magnesium chloride (4.54 g, 47.8 mmol) and THF (50 mL) and while maintaining the temperature of this solution at 5 to 15° C., t-butylmagnesium chloride (2 M solution in THF, 15.9 mL, 31.8 mmol) was added, followed by 1.5 hours of further stirring at that temperature.

While maintaining the temperature of that solution at 5 to 15° C., a solution of lithium aluminum hydride (1.81 g, 47.8 mmol) in THF (10 mL) was added and, thereafter, the mixture was heated under reflux with stirring for 6 hours. The reaction mixture was then cooled to 5° C., water (100 mL) was added, and the mixture was further stirred at room temperature for 0.5 hour.

Figure 5:
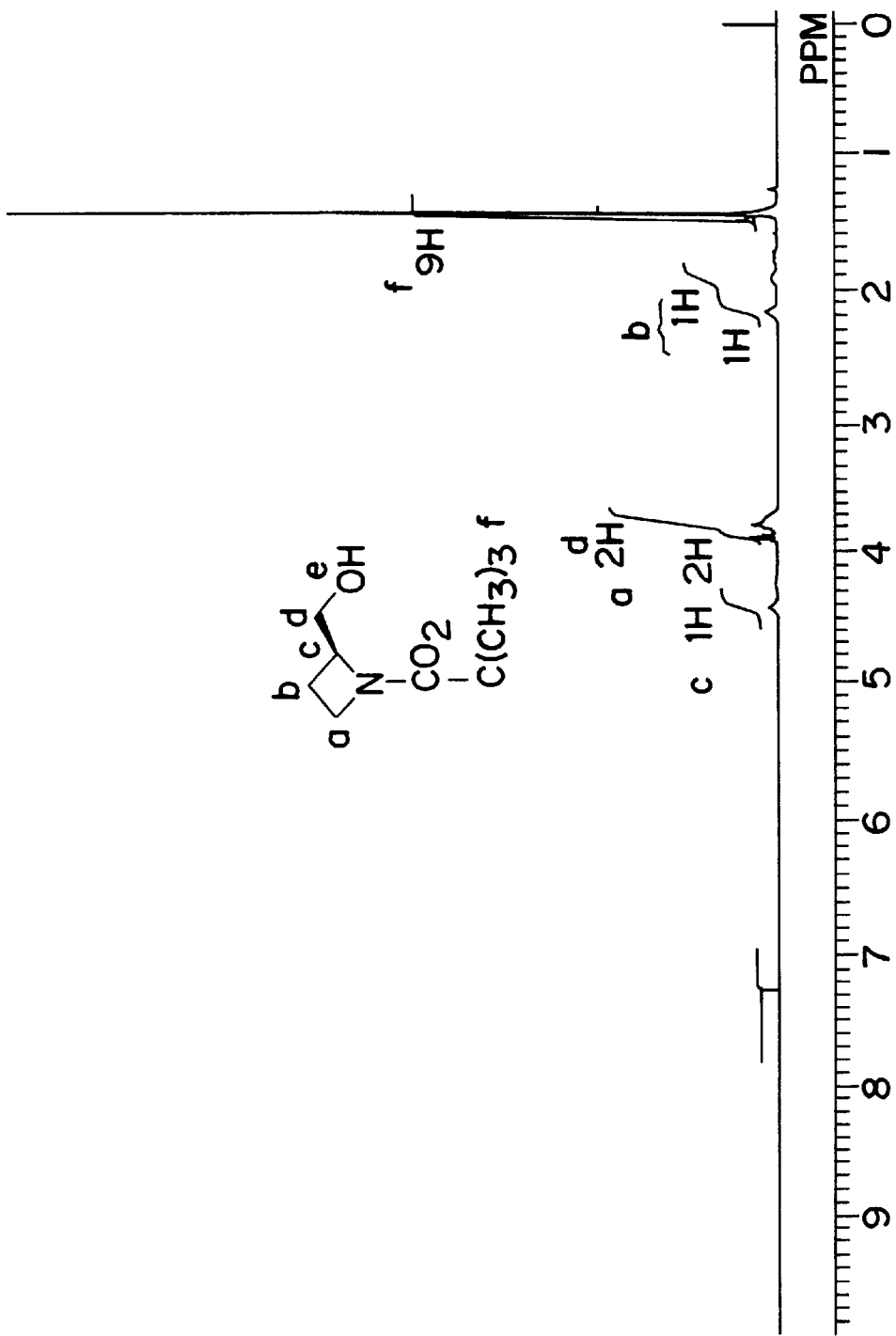
FIG. 5 is a proton NMR spectrum (solvent: $CDCl_3$) of the (S)-N-t-butoxycarbonylazetidine-2-methanol obtained in Example 5.

This solution of (S)-azetidine-2-methanol was adjusted to pH 10 by adding 10% sulfuric acid, sodium hydrogen carbonate (3.37 g, 31.8 mmol) was then added, and di-t-butyl dicarbonate (7.63 g, 35.0 mmol) was added at room temperature. Thereafter, stirring was continued for 14 hours. The reaction mixture was adjusted to pH 7 and extracted with ethyl acetate (50 mL×2), and the extract was washed with water (50 mL×1), dried over magnesium sulfate and filtered. The filtrate was concentrated and subjected to column chromatography (Wakogel C-200) using toluene/ethyl acetate (1/1) as a mobile phase for separation/purification, to give an oil (5.77 g). Based on its proton NMR spectrum (FIG. 5), said oil was identified as the desired product (S)-N-t-butoxycarbonylazetidine-2-methanol (yield 97.0%).

EXAMPLE 6

Synthesis of (S)-N-benzyloxycarbonylazetidine-2-methanol

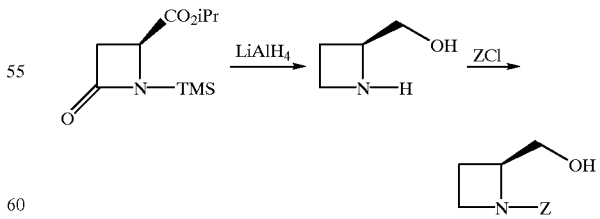

In a nitrogen gas atmosphere, a reaction flask was charged with the isopropyl (2S)-4-oxo-1-trimethylsilyl-2-azetidinecarboxylate obtained in Reference Example 3 (1.04 g, 4.54 mmol), magnesium chloride (1.43 g, 15.0 mmol) and THF (10 mL) and, while maintaining the temperature of this solution at 5 to 15° C., lithium aluminum hydride (0.249 g, 6.55 mmol) was added and, thereafter, the mixture was heated under reflux with stirring for 6 hours. The reaction mixture was cooled to 5° C., water (30 mL) was added and the mixture was further stirred at room temperature for 0.5 hour. This solution was submitted to the next step without isolating/purifying (S)-azetidine-2-methanol therefrom.

Said solution of (S)-azetidine-2-methanol was adjusted to pH 10 by adding 10% sulfuric acid, sodium hydrogen carbonate (0.873 g, 10.5 mmol) was then added and benzyloxycarbonyl chloride (1.75 g, 10.5 mmol) was added at room temperature. Thereafter, stirring was continued for 14 hours. The reaction mixture was adjusted to pH 7 and extracted with ethyl acetate (50 mL×2), the extract was washed with water (50 mL×1), dried over magnesium sulfate and filtered, and the filtrate was concentrated. The concentrate was subjected to column chromatography (Wakogel C-200) using toluene/ethyl acetate as a mobile phase for separation/purification, to give (S)-N-benzyloxycarbonylazetidine-2-methanol as a pale yellow oil (0.495 g, yield 49%). As a byproduct, (S)- 2-N-benzyloxycarbonyl-1,4-butanediol was obtained (0.26 g, yield 24%).

EXAMPLE 7

Synthesis of (S)-N-benzyloxycarbonylazetidine-2-methanol (Effect of Magnesium Fluoride, Magnesium Chloride and Tetra-n-butylammonium Fluoride)

In a nitrogen gas atmosphere, a reaction flask was charged with the isopropyl (2S)-4-oxo-1-trimethylsilyl-2-azetidinecarboxylate obtained in Reference Example 3 (0.541 g, 2.36 mmol), magnesium chloride (0.562 g, 5.90 mmol), magnesium fluoride (0.147 g, 2.36 mmol) and THF (10 mL). To this solution was added, at 5° C., tetra-n-butylammonium fluoride (1 M solution in THF, 0.24 mL, 0.24 mmol), and the mixture was stirred at 5° C. for 1 hour and then at 15° C. for 1 hour. Then, while maintaining this solution at 5 to 15° C., lithium aluminum hydride (0.179 g, 4.72 mmol) was added and, then, the mixture was heated under reflux with stirring for 6 hours. The reaction mixture was cooled to 5° C., water (15 mL) was added, and the mixture was stirred at room temperature for 0.5 hour. This solution was submitted to the next step without isolating/purifying (S)-azetidine-2-methanol therefrom.

Said solution of (S)-azetidine-2-methanol was adjusted to pH 10 by adding 10% sulfuric acid, sodium hydrogen carbonate (0.44 g, 5.29 mmol) was then added, and benzyloxycarbonyl chloride (0.88 g, 5.16 mmol) was added thereto at room temperature, followed by 14 hours of stirring. The solution was adjusted to pH 7 and extracted with ethyl acetate (50 mL ×2), the extract was washed with water (50 mL×1), dried over magnesium sulfate and filtered, and the filtrate was concentrated. The concentrate was subjected to column chromatography (Wakogel C-200) using toluene/ethyl acetate (1/1) as a mobile phase for separation/purification, to give (S)-N-benzyloxycarbonylazetidine-2-methanol (0.499 g, yield 96%) as a pale yellow oil. (S)-2-N-benzyloxycarbonyl-1,4-butanediol was obtained as a byproduct (0.032 g, yield 6%).

EXAMPLE 8

Synthesis of (S)-N-benzyloxycarbonylazetidine-2-methanol (Effect of Magnesium Fluoride, Magnesium Chloride and tetra-n-butylammonium Bromide)

In a nitrogen gas atmosphere, a reaction flask was charged with the isopropyl (2S)-4-oxo-1-trimethylsilyl-2-azetidinecarboxylate obtained in Reference Example 3 (1.078 g, 4.71 mmol), magnesium chloride (1.12 g, 7.07 mmol), magnesium fluoride (0.294 g, 4.71 mmol) and THF (10 mL). To this solution was added, at 5° C., tetra-n-butylammonium bromide (0.152 mL, 0.471 mmol), and the mixture was stirred at 5° C. for 1 hour and then at 15° C. for 1 hour. Then, while maintaining this solution at 5 to 15° C., lithium aluminum hydride (0.360 g, 9.44 mmol) was added and, then, the mixture was heated under reflux with stirring for 6 hours. The reaction mixture was cooled to 5° C., water (30 mL) was added, and the mixture was stirred at room temperature for 0.5 hour. This solution was submitted to the next step without isolating/purifying (S)-azetidine-2-methanol therefrom.

Said solution of (S)-azetidine-2-methanol was adjusted to pH 10 by adding 10% sulfuric acid, sodium hydrogen carbonate (0.88 g, 10.5 mmol) was then added, and benzyloxycarbonyl chloride (1.76 g, 10.3 mmol) was added thereto at room temperature, followed by 14 hours of stirring. The solution was adjusted to pH 7 and extracted with ethyl acetate (50 mL ×2), the extract was washed with water (50 mL×1), dried over magnesium sulfate and filtered, and the filtrate was concentrated. The concentrate was subjected to column chromatography (Wakogel C-200) using toluene/ethyl acetate (1/1) as a mobile phase for separation/purification, to give (S)-N-benzyloxycarbonylazetidine-2-methanol (0.781 g, yield 75%) as a pale yellow oil. (S)-2-N-benzyloxycarbonyl-1,4-butanediol was obtained as a byproduct (0.096 g, yield 9%).

EXAMPLE 9

Synthesis of (S)-N-benzyloxycarbonylazetidine-2-carboxylic Acid

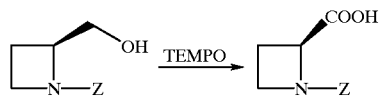

Figure 6:
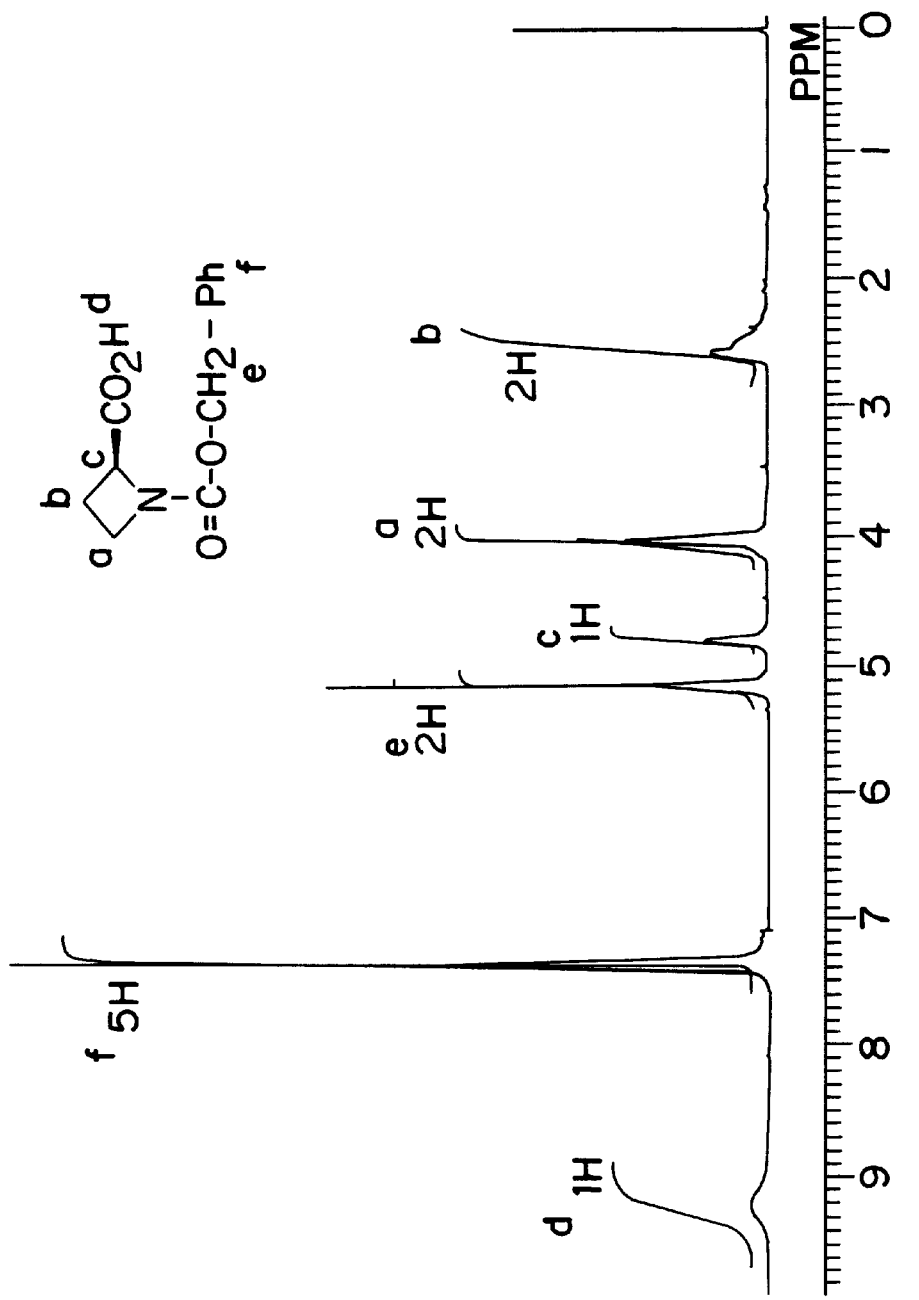
FIG. 6 is a proton NMR spectrum (solvent: $CDCl_3$) of the (S)-N-benzyloxycarbonylazetidine-2-carboxylic acid obtained in Example 9.

A reaction flask was charged with the (S)-N-benzyloxycarbonylazetidine-2-methanol (2.21 g, 10.0 mmol) obtained in Example 2, TEMPO (15.6 mg, 0.1 mmol), NaBr (3.09 g, 30.0 mmol), ethyl acetate (20 mL) and water (4 mL). Thereto was added, at 5 to 10° C., a mixture of an aqueous solution of sodium hypochlorite (Nakalai Tesque, 50 mL) and sodium hydrogen carbonate (2.94 g, 35.0 mmol). Stirring was further continued for 3 hours. Sodium thiosulfate (0.50 g, 3.2 mmol) was added to the reaction mixture, and the mixture was stirred for 5 minutes. Then, the reaction mixture was adjusted to pH 2 by adding 10% sulfuric acid and extracted with ethyl acetate (50 mL×2), the organic layer was washed with water (50 mL×2), dried over magnesium sulfate and filtered, and the filtrate was concentrated to give a pale yellow oil (2.12 g). Based on its proton NMR spectrum (FIG. 6), this was identified as the desired product (S)-N-benzyloxycarbonylazetidine-2-carboxylic acid (yield 90.0%).

Analysis of the product for optical purity using a chiral column (CHIRALCEL, OD-R, product of Daicel Chemical Industries) revealed that its optical purity was 99.2% ee.

EXAMPLE 10

Synthesis of (S)-N-t-butoxycarbonylazetidine-2-carboxylic Acid

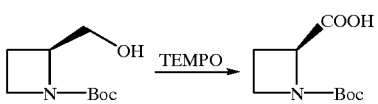

Figure 7:
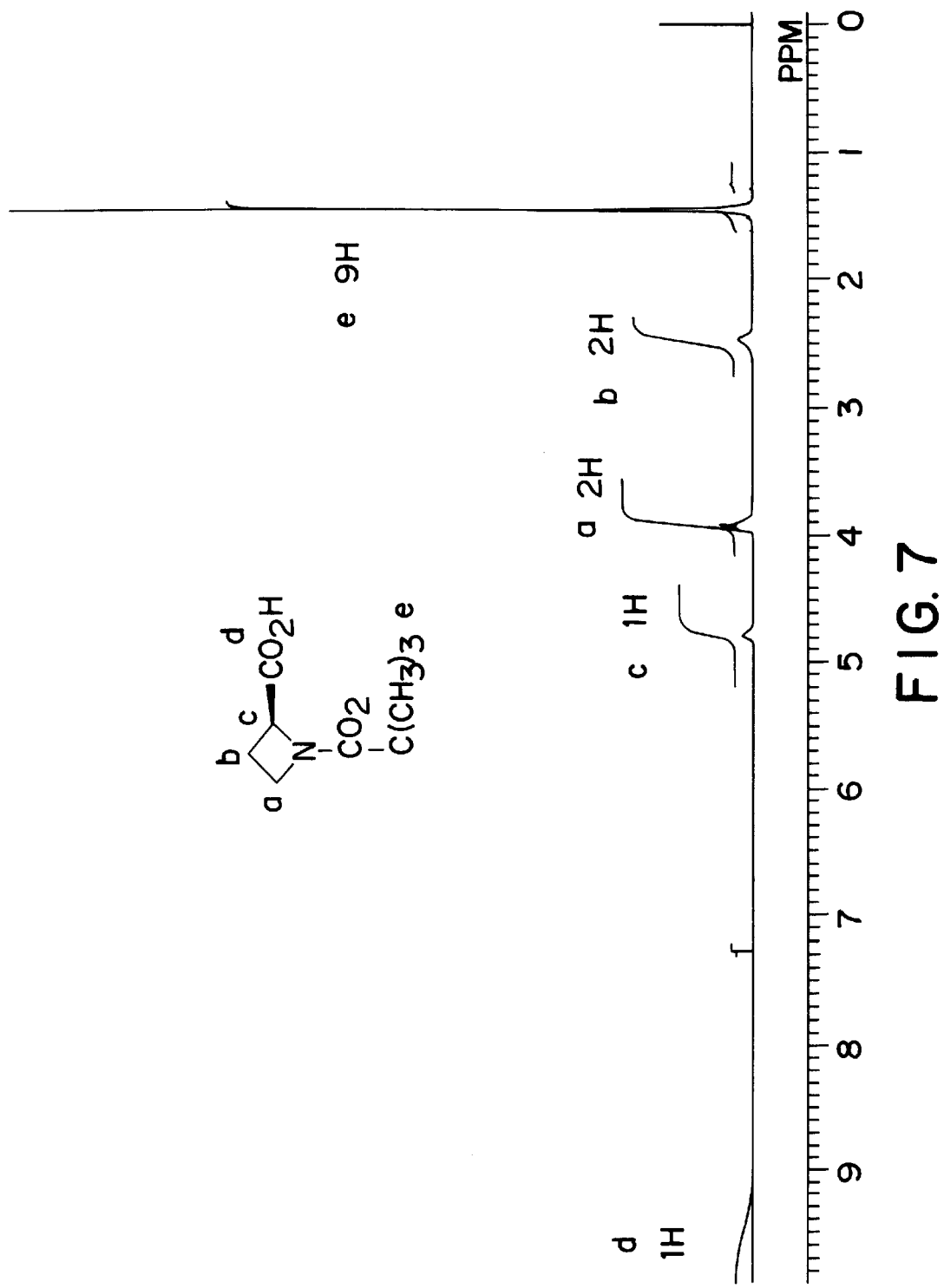
FIG. 7 is a proton NMR spectrum (solvent: $CDCl_3$) of the (S)-N-t-butoxycarbonylazetidine-2-carboxylic acid obtained in Example 10.

A reaction flask was charged with the (S)-N-t-butoxycarbonylazetidine-2-methanol (2.97 g, 15.9 mmol) obtained in Example 5, TEMPO (25.0 mg, 0.159 mmol), NaBr (4.94 g, 47.7 mmol), ethyl acetate (35 mL) and water (7 mL). Thereto was added, at 5 to 10° C., a mixture of an aqueous solution of sodium hypochlorite (Nakalai Tesque, 80 mL) and sodium hydrogen carbonate (4.68 g, 55.7 mmol). Stirring was further continued for 3 hours. Sodium thiosulfate (0.79 g, 5.06 mmol) was added to the reaction mixture, and the mixture was stirred for 5 minutes. Then, the reaction mixture was adjusted to pH 2 by adding 10% sulfuric acid and extracted with ethyl acetate (50 mL×2), the organic layer was washed with water (50 mL×2), dried over magnesium sulfate and filtered, and the filtrate was concentrated to give white crystals (3.18 g). Based on its proton NMR spectrum (FIG. 7), this was identified as the desired product (S)-N-benzyloxycarbonylazetidine-2-carboxylic acid (yield 99.2%).

Upon analysis of the product for optical purity using a chiral column (Chiralcel, OD-R, Daicel Chemical Industries), (S)-N-benzyloxycarbonylazetidine-2-carboxylic acid alone was detected. (R)-N-benzyloxycarbonylazetidine-2-carboxylic acid was not detected.

EXAMPLE 11

Synthesis of (S)-azetidine-2-carboxylic Acid

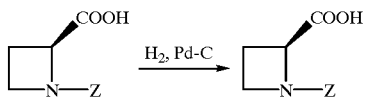

Figure 8:
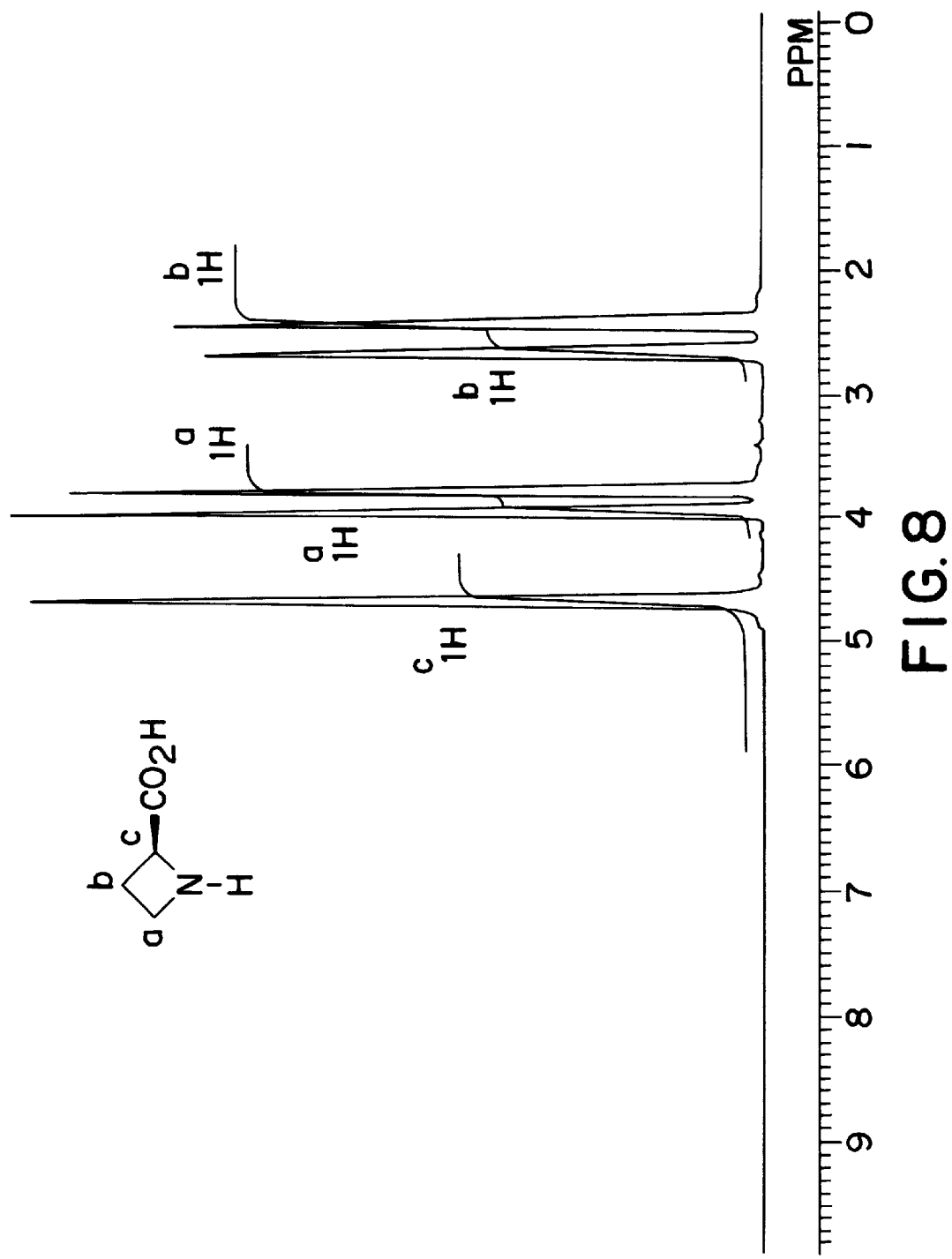
FIG. 8 is a proton NMR spectrum (solvent: $D_2O$) of the (S)-azetidine-2-carboxylic acid obtained in Example 11.

A reaction flask was charged with the (S)-N-benzyloxycarbonylazetidine-2-carboxylic acid obtained in Example 8 (1.50 g, 6.38 mmol), palladium carbon (10%, 497 mg) and methanol (15 mL), and the mixture was stirred in a hydrogen gas atmosphere at 25° C. for 3 hours. The palladium carbon was filtered off and washed with water, The filtrate and washings were combined and concentrated to give white crystals (0.58 g). Based on its proton NMR spectrum (FIG. 8), this product was identified as the desired product (S)-azetidine-2-carboxylic acid (yield 90%).

INDUSTRIAL APPLICABILITY

The process for producing azetidine-2-carboxylic acid and intermediates thereof, which is constituted as mentioned above, is efficient and economical. Therefore, it can advantageously be conducted on a commercial scale. Further, racemization does not occur in the production steps. It is thus possible to produce optically active azetidine-2-methanol and optically active azetidine-2-carboxylic acid from the corresponding optically active 4-oxo-2-azetidinecarboxylic acid derivative, which is readily obtainable from optically active aspartic acid.

What is claimed is:

1. A process for producing azetidine-2-carboxylic acid of the following formula (5):

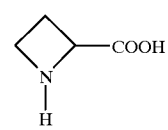

(5)

which comprises subjecting a 4-oxo-2-azetidinecarboxylic acid derivative represented by the following general formula (1)

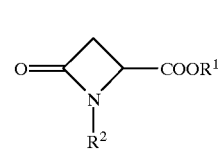

(1)

to hydride reduction to give azetidine-2-methanol of the following formula (2):

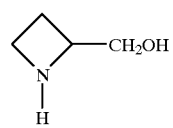

(2)

treating the same with an amino-protecting agent to give an N-protected azetidine-2-methanol represented by the following general formula (3):

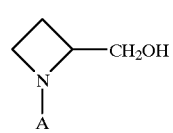

(3)

(in the formula, A represents an amino-protecting group), treating this with an oxidizing agent to give an N-protected azetidine-2-carboxylic acid represented by the following general formula (4):

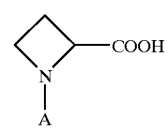

(4)

(in the formula, A is as defined above), and, further, subjecting the amino protecting group thereof to elimination.

2. The process for producing azetidine-2-carboxylic acid according to claim 1, wherein $R^1$ is methyl, ethyl, n-propyl, isopropyl, n-butyl, isobutyl, t-butyl or benzyl.

3. The process for producing azetidine-2-carboxylic acid according to claim 1, wherein A is benzyloxycarbonyl, methoxycarbonyl, ethoxycarbonyl or t-butoxycarbonyl.

4. The process for producing azetidine-2-carboxylic acid according to claim 1, wherein optically active (S)-azetidine-2-carboxylic acid is produced from an optically active (S)-4-oxo-2-azetidinecarboxylic acid derivative or optically active (R)-azetidine-2-carboxylic acid is produced from an optically active (R)-4-oxo-2-azetidinecarboxylic acid derivative.

5. The process for producing azetidine-2-carboxylic acid according to claim 1, wherein the hydride reduction of the 4-oxo-2-azetidinecarboxylic acid derivative of the general formula (1) is carried out after preliminary treatment of said 4-oxo-2-azetidinecarboxylic acid derivative with a Grignard reagent, or in the presence of a magnesium salt, or in the presence of a magnesium salt after preliminary treatment of said 4-oxo-2-azetidinecarboxylic acid derivative with a Grignard reagent.

6. The process for producing azetidine-2-carboxylic acid according to claim 1, wherein the hydride reduction of the 4-oxo-2-azetidinecarboxylic acid derivative of the general formula (1) is carried out using lithium aluminum hydride as a reducing agent.

7. The process for producing azetidine-2-carboxylic acid according to claim 1, wherein the hydride reduction of the 4-oxo-2-azetidinecarboxylic acid derivative of the general formula (1) in which $R^2$ in the general formula (1) is a silyl group represented by the formula

(in the formula, $R^6$, $R^7$ and $R^8$ are the same or different, and each represents an alkyl group containing 1 to 30 carbon atoms, an aryl group containing 6 to 35 carbon atoms or an aralkyl group containing 7 to 36 carbon atoms) is carried out after preliminary treatment of said 4-oxo-2-azetidinecarboxylic acid derivative with a magnesium salt, a fluoride salt and a quaternary ammonium halide.

8. A process for producing an N-protected azetidine-2-carboxylic acid represented by the following general formula (4):

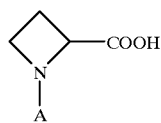

(in the formula, A represents an amino-protecting group), which comprises subjecting a 4-oxo-2-azetidinecarboxylic acid derivative represented by the general formula (1):

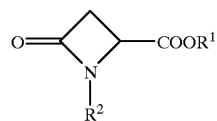

to hydride reduction to give azetidine-2-methanol of the following formula (2):

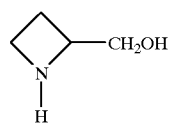

treating the same with an amino-protecting agent to give N-protected azetidine-2-methanol represented by the following general formula (3):

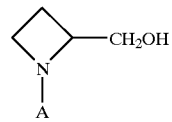

(in the formula, A is as defined above), and treating this with an oxidizing agent.

9. The process for producing an N-protected azetidine-2-carboxylic acid according to claim 8, wherein $R^1$ is methyl, ethyl, n-propyl, isopropyl, n-butyl, isobutyl, t-butyl or benzyl.

10. The process for producing an N-protected azetidine-2-carboxylic acid according to claim 8, wherein A is benzyloxycarbonyl, methoxycarbonyl, ethoxycarbonyl or t-butoxycarbonyl.

11. The process for producing an N-protected azetidine-2-carboxylic acid according to claim 8, wherein an optically active (S)-N-protected azetidine-2-carboxylic acid is produced from an optically active (S)-4-oxo-2-azetidinecarboxylic acid derivative or an optically active (R)-N-protected azetidine-2-carboxylic acid is produced from an optically active (R)-4-oxo-2-azetidinecarboxylic acid derivative.

12. The process for producing an N-protected azetidine-2-carboxylic acid according to claim 8, wherein the hydride reduction of the 4-oxo-2-azetidinecarboxylic acid derivative of the general formula (1) is carried out after preliminary treatment of said 4-oxo-2-azetidinecarboxylic acid derivative with a Grignard reagent, or in the presence of a magnesium salt, or in the presence of a magnesium salt after preliminary treatment of said 4-oxo-2-azetidinecarboxylic acid derivative with a Grignard reagent.

13. The process for producing an N-protected azetidine-2-carboxylic acid according to claim 8, wherein the hydride reduction of the 4-oxo-2-azetidinecarboxylic acid derivative of the general formula (1) is carried out using lithium aluminum hydride as a reducing agent.

14. The process for producing an N-protected azetidine-2-carboxylic acid according to claim 8, wherein the hydride reduction of the 4-oxo-2-azetidinecarboxylic acid derivative of the general formula (1) in which $R^2$ in the general formula (1) is a silyl group represented by the formula

(in the formula, $R^6$, $R^7$ and $R^8$ are the same or different, and each represents an alkyl group containing 1 to 30 carbon atoms, an aryl group containing 6 to 35 carbon atoms or an aralkyl group containing 7 to 36 carbon atoms) is carried out after preliminary treatment of said 4-oxo-2-azetidinecarboxylic acid derivative with a magnesium salt, a fluoride salt and a quaternary ammonium halide.

15. A process for producing an N-protected azetidine-2-methanol represented by the following general formula (3):

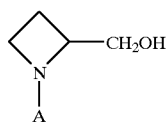

(in the formula, A represents an amino-protecting group), which comprises subjecting a 4-oxo-2-azetidinecarboxylic acid derivative represented by the following general formula (1):

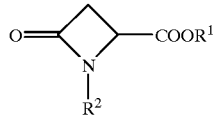

to hydride reduction to give azetidine-2-methanol of the following formula (2):

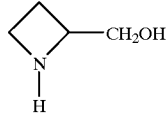

and treating the same with an amino-protecting agent.

16. The process for producing an N-protected azetidine-2-methanol according to claim 15, wherein $R^1$ is methyl, ethyl, n-propyl, isopropyl, n-butyl, isobutyl, t-butyl or benzyl.

17. The process for producing an N-protected azetidine-2-methanol according to claim 15, wherein A is benzyloxycarbonyl, methoxycarbonyl, ethoxycarbonyl or t-butoxycarbonyl.

18. The process for producing an N-protected azetidine-2-methanol according to claim 15, wherein an optically active (S)-N-protected azetidine-2-methanol is produced from an optically active (S)-4-oxo-2-azetidinecarboxylic acid derivative or an optically active (R)-N-protected azetidine-2-methanol is produced from an optically active (R)-4-oxo-2-azetidinecarboxylic acid derivative.

19. The process for producing an N-protected azetidine-2-methanol according to claim 15, wherein the reduction of the 4-oxo-2-azetidinecarboxylic acid derivative of the general formula (1) is carried out after preliminary treatment of said 4-oxo-2-azetidinecarboxylic acid derivative with a Grignard reagent, or in the presence of a magnesium salt, or in the presence of a magnesium salt after preliminary treatment of said 4-oxo-2-azetidinecarboxylic acid derivative with a Grignard reagent.

20. The process for producing an N-protected azetidine-2-methanol according to claim 15, wherein the hydride reduction of the 4-oxo-2-azetidinecarboxylic acid derivative of the general formula (1) is carried out using lithium aluminum hydride as a reducing agent.

21. The process for producing an N-protected azetidine-2-methanol according to claim 15, wherein the hydride reduction of the 4-oxo-2-azetidinecarboxylic acid derivative of the general formula (1) in which $R^2$ in the general formula (1) is a silyl group represented by the formula $SiR^6R^7R^8$ (in the formula, $R^6$, $R^7$ and $R^8$ are the same or different, and each represents an alkyl group containing 1 to 30 carbon atoms, an aryl group containing 6 to 35 carbon atoms or an aralkyl group containing 7 to 36 carbon atoms) is carried out after preliminary treatment of said 4-oxo-2-azetidinecarboxylic acid derivative with a magnesium salt, a fluoride salt and a quaternary ammonium halide.

22. A process for producing azetidine-2-methanol of the following formula (2):

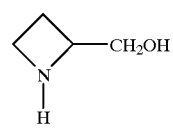

which comprises subjecting a 4-oxo-2-azetidinecarboxylic acid derivative represented by the following general formula (1):

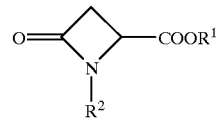

to hydride reduction.

23. The process for producing azetidine-2-methanol according to claim 22, wherein $R^1$ is methyl, ethyl, n-propyl, isopropyl, n-butyl, isobutyl, t-butyl or benzyl.

24. The process for producing azetidine-2-methanol according to claim 22, wherein optically active (S)-azetidine-2-methanol is produced from an optically active (S)-4-oxo-2-azetidinecarboxylic acid derivative or optically active (R)-azetidine-2-methanol is produced from an optically active (R)-4-oxo-2-azetidinecarboxylic acid derivative.

25. The process for producing azetidine-2-methanol according to claim 22, wherein the reduction of the 4-oxo-2-azetidinecarboxylic acid derivative of the general formula (1) is carried out after preliminary treatment of said 4-oxo-2-azetidinecarboxylic acid derivative with a Grignard reagent, or in the presence of a magnesium salt, or in the presence of a magnesium salt after preliminary treatment of said 4-oxo-2-azetidinecarboxylic acid derivative with a Grignard reagent.

26. The process for producing azetidine-2-methanol according to claim 22, wherein the hydride reduction of the 4-oxo-2-azetidinecarboxylic acid derivative of the general formula (1) is carried out using lithium aluminum hydride as a reducing agent.

27. The process for producing azetidine-2-methanol according to claim 22, wherein the hydride reduction of the 4-oxo-2-azetidinecarboxylic acid derivative of the general formula (1) in which $R^2$ in the general formula (1) is a silyl group represented by the formula $SiR^6R^7R^8$ (in the formula, R6, $R^7$ and $R^8$ are the same or different, and each represents an alkyl group containing 1 to 30 carbon atoms, an aryl group containing 6 to 35 carbon atoms or an aralkyl group containing 7 to 36 carbon atoms) is carried out after preliminary treatment of said 4-oxo-2-azetidinecarboxylic acid derivative with a magnesium salt, a fluoride salt and a quaternary ammonium halide.

* * * * *